United States Patent [19]

Darms et al.

[11] 4,158,662

[45] Jun. 19, 1979

[54] PHTHALIMIDES SUBSTITUTED BY ALKENYLAMINO GROUPS

[75] Inventors: Roland Darms, Therwil; Hubert Meindl, Riehen, both of Switzerland

[73] Assignee: Ciba-Geigy Corporation, Ardsley, N.Y.

[21] Appl. No.: 857,156

[22] Filed: Dec. 5, 1977

[30] Foreign Application Priority Data

Dec. 14, 1976 [CH] Switzerland .................. 15704/76

[51] Int. Cl.² .................. C07D 403/12; C07D 403/10; C07D 209/48
[52] U.S. Cl. .................. 260/326 N; 260/326 S; 526/263; 562/457
[58] Field of Search .................. 260/326 N, 326 S

[56] References Cited

U.S. PATENT DOCUMENTS

| | | | |
|---|---|---|---|
| 3,380,964 | 4/1968 | Grun der beber | 260/47 |
| 3,528,950 | 9/1970 | Lubowitz | 260/78.4 |
| 3,533,996 | 10/1970 | Grun der beber | 260/47 |
| 3,562,223 | 2/1971 | Bargain et al. | 260/78 |
| 4,035,345 | 7/1977 | Ducloux | 260/78 DA |

OTHER PUBLICATIONS

Bargain et al. II, 960 (1977).
Bargain et al. III, Chem. Abs. 78, 148589e.
Takeda et al., Chem. Abs. 55, 508g (1960).

*Primary Examiner*—Mark L. Berch
*Attorney, Agent, or Firm*—Luther A. R. Hall

[57] ABSTRACT

Novel phthalimides substituted by alkenylamino groups, processes for their preparation and hot-curable mixtures which are stable on storage and contain at least one phthalimide according to the invention and a polyimide which has at least two groupings containing a C=C double bond are described. These hot-curable mixtures which are stable on storage are distinguished by improved processing characteristics, in particular a prolonged pot life, and are suitable for the production of various mouldings and especially also for the production of complicated castings.

5 Claims, No Drawings

PHTHALIMIDES SUBSTITUTED BY ALKENYLAMINO GROUPS

The present invention relates to novel phthalimides substituted by alkenylamino groups, processes for their preparation and hot-curable mixtures which are stable on storage and contain at least one phthalimide according to the invention and a polyimide which has at least two groupings containing a carbon-carbon double bond.

Heat-curable resins which are obtained by a polyaddition reaction of a N,N'-bis-imide of an unsaturated dicarboxylic acid with primary diamines and the curing of these resins or pre-adducts by polymerisation by the action of heat are described in French Patent Specification 1,555,564. However, these resins are not suitable for the production of complicated castings since the starting mixtures of bis-imide and diamine must be heated in order to achieve an adequately low viscosity and the processing times are greatly shortened as a result.

Heat-curable compositions, for the production of mouldings, which contain a reaction product of a N,N'-bis-imide of an unsaturated dicarboxylic acid having two carbon-carbon double bonds, a polyamine and a further monomer having a carbon-carbon double bond which can be polymerised by heating are described in German Offenlegungsschrift 2,131,735. In these compositions, the last-mentioned monomer can also be, inter alia, an allyl derivative, for example an allyl ester, or an allyl ether, or an aromatic or heterocyclic compound containing an allyl substituent, especially allyl o-phthalate, allyl cyanurate or triallyl trimellitate. The said allyl compounds are apparently added in order to reduce the viscosity of the starting mixtures (bis-imide+polyamine). However, as a result mixtures are obtained which, because of the relatively short processing time, are not very suitable for the production of complicated castings, for filling cavities or gaps and for embedding bodies in so-called throwaway moulds. If it is desired to increase the time during which the compositions can be used in the molten, castable state, i.e. the processing time or the so-called pot life, it is necessary to add aromatic compounds having 2-4 benzene rings, as polymerisation regulators, in an amount of up to 10 percent by weight, relative to the composition of bis-imide, polyamine and monomer, so that a total of at least four different components is required for these heat-curable compositions.

The object of the invention was, therefore, to provide hot-curable mixtures which are stable on storage and have improved processing characteristics by a simpler route and avoiding the above disadvantages.

Accordingly, the invention relates to novel phthalimides of the formula I

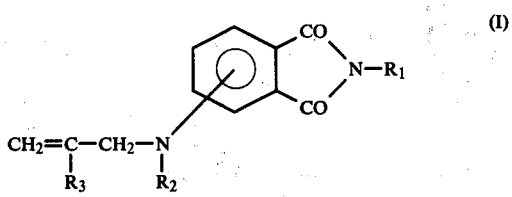

(I)

in which $R_1$ is alkyl having 1-12 carbon atoms, alkenyl having 2-5 carbon atoms, aryl having 6-10 carbon atoms in the aryl part, alkylene-Y having 2-12 carbon atoms in the alkylene part, arylene-Y having 6-10 carbon atoms in the arylene part or a grouping

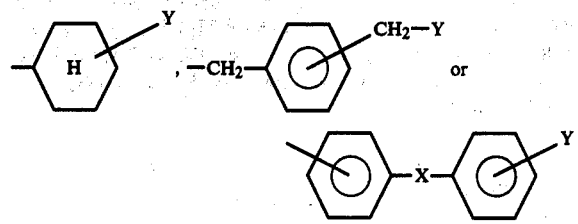

in which X is —$CH_2$—, —S—, —SO—, —$SO_2$—, —O— or

and Y is a grouping

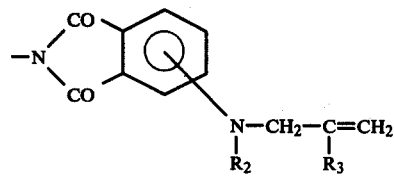

$R_2$ is hydrogen or

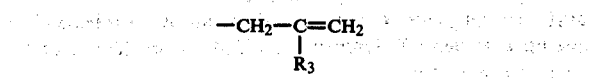

and $R_3$ is hydrogen or methyl.

The phthalimides of the formula I can also be in the form of mixtures of the 3- and 4-isomers.

Using the phthalimides, according to the invention, of the formula I and polyimides which have at least two groupings containing a carbon-carbon double bond, it is possible, surprisingly, without the addition of polymerisation regulators or the like, to prepare hot-curable mixtures which are stable on storage and which, without a perceptible impairment of their viscosity or of the mechanical and electrical properties of the products which can be produced therefrom, have an adequately long processing time, so that they can also be used for the production of complicated castings.

The phthalimides, according to the invention, of the formula I can be prepared by reacting a compound of the formula II

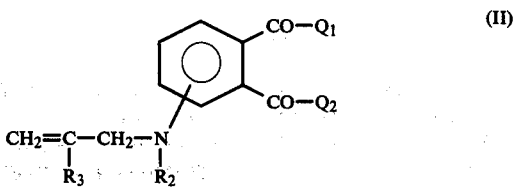

(II)

in which $Q_1$ and $Q_2$ are —OH, or $Q_1$ and $Q_2$ together form the grouping —O—, and $R_2$ and $R_3$ are as defined under formula I, with a compound of the formula III $$H_2N-R_1' \quad (III)$$

in which $R_1'$ is alkyl having 1–12 carbon atoms, alkenyl having 2–5 carbon atoms, aryl having 6–10 carbon atoms in the aryl part, alkylene—$NH_2$ having 2–12 carbon atoms in the alkylene part, arylene—$NH_2$ having 6–10 carbon atoms in the arylene part or a grouping of the formulae

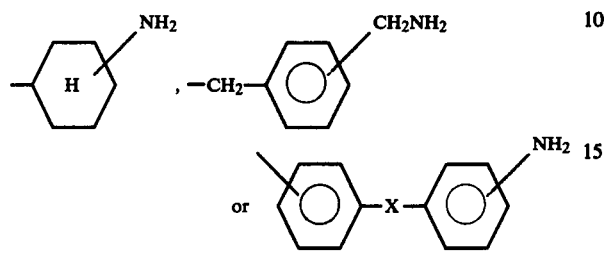

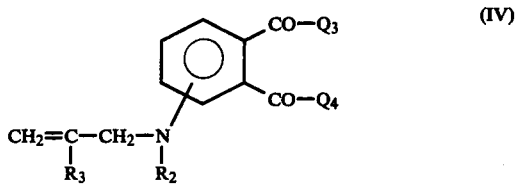

in which X is as defined under formula I, to give a compound of the formula IV

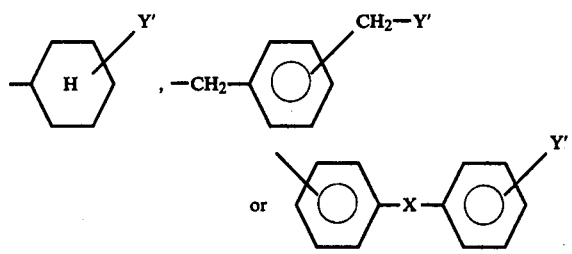

in which one of $Q_3$ and $Q_4$ is —OH and the other is —NH—$R_1''$, $R_1''$ is alkyl having 1–12 C atoms, alkenyl having 2–5 C atoms, aryl having 6–10 C atoms in the aryl part, alkylene-Y' having 2–12 C atoms in the alkylene part, arylene-Y' having 6–10 C atoms in the arylene part or a grouping

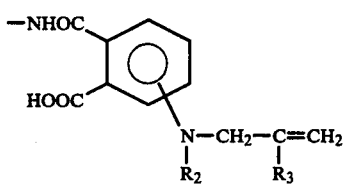

and Y' is a grouping

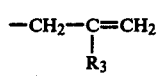

and X, $R_2$ and $R_3$ are as defined under formula I, and cyclising the compound of the formula IV.

Phthalimides of the formula I in which $R_1$ is alkenyl having 2–5 carbon atoms and especially a grouping $$-CH_2-C=CH_2$$
$$\quad\quad\quad |$$
$$\quad\quad\quad R_3$$

can also be prepared by reacting a compound of the formula V

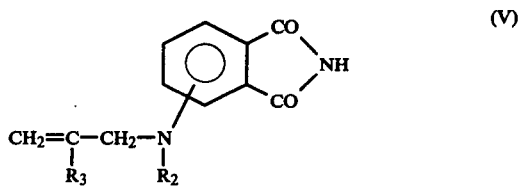

in the presence of an inorganic or organic base with an alkenyl halide of the formula VI

in which formula Hal is preferably chlorine or bromine, the alkenyl group has 2–5 carbon atoms and $R_2$ and $R_3$ are as defined above.

Groups according to the definition which are represented by $R_1$, $R_1'$ or $R_1''$ can be unsubstituted or substituted, for example by halogen atoms, such as chlorine, fluorine or bromine, or alkyl or alkoxy groups having 1–4, and especially 1 or 2, carbon atoms.

Alkyl and alkenyl groups $R_1$, $R_1'$ and $R_1''$ and also the alkylene parts in the said substituents can be straight-chain or branched. Possible alkyl groups $R_1$, $R_1'$ or $R_1''$ are, in particular, unsubstituted alkyl groups having 1–12, preferably 1–8 and especially 1–4, carbon atoms. Examples which may be mentioned are: the methyl, ethyl, n-propyl, isopropyl, n-butyl, tert.-butyl, n-heptyl, n-hexyl, n-octyl and n-dodecyl group.

Alkenyl group $R_1$, $R_1'$ or $R_1''$ are preferably unsubstituted. Such groups are especially the methallyl group and in particular the allyl group. Possible aryl groups $R_1$, $R_1'$ and $R_1''$ are, for example, phenyl groups optionally substituted by halogen atoms, such as chlorine, fluorine or bromine, or by alkyl or alkoxy groups having 1–4 and especially 1 or 2 carbon atoms, and unsubstituted naphthyl groups. Unsubstituted phenyl groups are preferred.

Alkylene parts in substituents $R_1$, $R_1'$ and $R_1''$ are preferably unsubstituted and in particular have 2–6 carbon atoms.

Arylene parts in substituents $R_1$, $R_1'$ and $R_1''$ are, in particular, phenylene groups, which are unsubstituted or substituted by a halogen atom or a methyl or methoxy group, and unsubstituted naphthylene groups.

Preferred groups

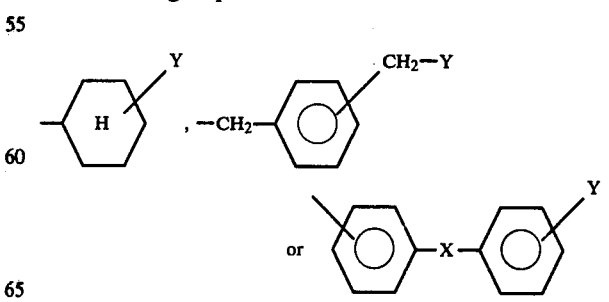

and corresponding amines of the formula III are those which follow:

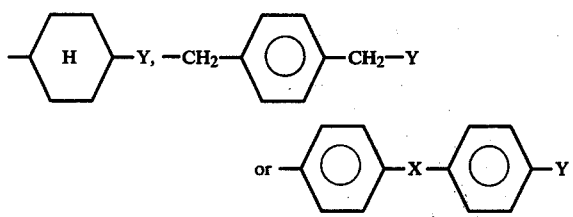

in which X is —SO₂ or

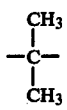

and especially —CH₂— or —O—.

R₂ is preferably —CH₂—CH=CH₂, whilst R₃ is especially hydrogen.

The groupings

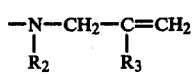

are preferably in the 3-position of the benzene ring. The phthalimides according to the invention and also the corresponding starting materials can, however, also be used in the form of mixtures of 3- and 4-alkenylamine-substituted compounds.

Particularly preferred phthalimides of the formula I are those in which R₁ is unsubstituted alkyl having 1–4 carbon atoms, allyl, phenyl or a grouping

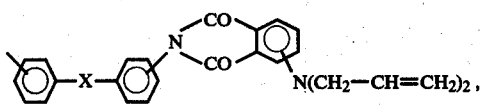

X is —CH₂— or —O—, R₂ is —CH₂—CH=CH₂ and R₃ is hydrogen.

The starting compounds of the formula II and V are novel and can be prepared as follows:

Compounds of the formula II

By reaction of aminophthalic acid derivatives of the formula VII

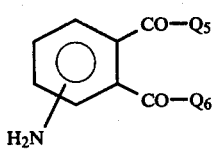

with a compound of the formula VIII

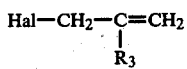

to give a phthalic acid derivative of the formula II′

$$\text{(II')}$$

and, if desired, conversion of the resulting phthalic acid of the formula II′ into another derivative of the formula II, for example to the corresponding anhydrides by chemical cyclisation or cyclisation by the action of heat, or, for the preparation of the corresponding mono-salts or half-esters, by reaction with suitable bases or alcohols, according to methods which are known per se.

In the above formulae VII, VIII and II′, Q₅ and Q₆ independently of one another are —OH or a group —O⁻M⁺ and Hal is a halogen atom, especially chlorine or bromine R₂ and R₃ are as defined under the formulae I and II, and M⁺ is an alkali metal cation, a trialkylammonium cation having 3–24 carbon atoms or a quaternary ammonium cation.

If Q₅ or Q₆ is a group —O⁻M⁺, M⁺ is, for example, the lithium, sodium, potassium, trimethylammonium, triethylammonium, methyl-diethylammonium or tri-n-octylammonium cation. Examples of quaternary ammonium cations M⁺ are the benzyltrimethylammonium and the tetramethylammonium cation. M⁺ is preferably the sodium cation.

Compounds of the formula V

By reaction of a phthalic acid derivative of the formula II′ with ammonia.

The starting compounds of the formula III and VI are known or can be prepared according to methods which are known per se.

The reaction of the compounds of the formula II with a compound of the formula III can be carried out in an inert organic solvent at temperatures between about 20° and 120° C. and especially at between about 40° and 80° C. or, alternatively, can be carried out in the melt. The compounds of the formula V are appropriately reacted with the halide of the formula VI in an organic medium. Suitable inert organic solvents are, for example, aromatic hydrocarbons, such as benzene, toluene and xylenes; aliphatic and cyclic ethers, such as diethyl ether, tetrahydrofurane, tetrahydropyrane and dioxane; dialkylsulphoxides, such as dimethylsulphoxide and diethylsulphoxide; N,N,N′,N′-tetramethylurea and tetrahydrothiophene dioxide (sulpholane). The preferred solvent is toluene.

The starting compounds of the formula II which are used are preferably the corresponding anhydrides.

Inorganic or organic bases which can be employed in the reaction of a compound of the formula V with a halide of the formula VI are, for example, tertiary amines, pyridine, alkaline earth metal carbonates, hydroxides or alcoholates having 1–4 carbon atoms in the alkyl part and alkali metal carbonates, hydroxides or alcoholates having 1–4 carbon atoms in the alkyl part, such as trimethylamine and triethylamine, pyridine, Mg carbonate, Ca carbonate, K carbonate and Na carbonate, Li hydroxide, K hydroxide and Na hydroxide, magnesium methylate, potassium ethylate and sodium ethylate, potassium tert.-butylate and sodium tert.-butylate.

The cyclisation of the compounds of the formula IV to the phthalimides of the formula I can be carried out in a manner which is known per se, chemically or by the action of heat. Chemical cyclisation is appropriately carried out at temperatures of about 40° to 120° C. in the presence of conventional dehydrating agents. Dehydrating agents which can be used are, in particular, anhydrides of aliphatic monocarboxylic acids having 2-5 carbon atoms, which are unsubstituted or substituted by halogen atoms or alkyl groups, such as acetic anhydride and propionic anhydride, trifluoroacetic anhydride, trimethylacetic anhydride or triethylacetic anhydride. Acetic anhydride is the preferred dehydrating agent. In general, however, cyclisation by the action of heat is preferred. For this purpose, the compounds of the formula IV are advantageously heated to temperatures between about 100° and 180° C. and preferably to temperatures between about 130° and 160° C.

After the reaction has ended, the phthalimides, according to the invention, of the formula I can be isolated and, if necessary, purified in a conventional manner, for example by distillation or recrystallisation from suitable organic solvents, such as mixtures of hydrocarbons.

The invention also relates to hot-curable mixtures which are stable on storage and contain (a) at least one phthalimide of the formula I, (b) at least one polyimide which has, per molecule, at least two radicals of the formula IX

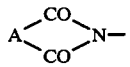 (IX)

in which A is a divalent radical containing a carbon-carbon double bond, and, if appropriate, (c) a polymerisation initiator and to a process for the preparation of crosslinked polymers containing imide groups by reacting at least one phthalimide of the formula I and at least one polyimide according to the definition with one another, if appropriate in the presence of a polymerisation initiator.

Most of the polyimides which can be employed according to the invention are described in the literature; c.f. for example, British Patent Specification No. 1,066,390, U.S. Pat. No. 3,528,950, French Patent Specification No. 1,555,564 and German Offenlegungsschriften 2,230,874 and 2,350,471.

Preferred polyimides are bis-imides of the formula X

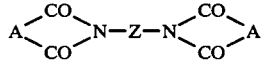 (X)

in which Z is a divalent bridge member having 2-30 carbon atoms and A is —CH=CH—,

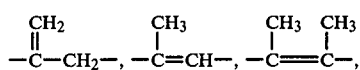

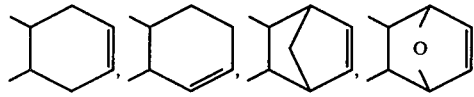

and especially

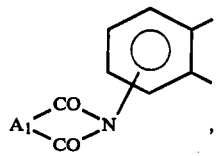

in which $A_1$ can have the same meanings as A with the exception of the last-mentioned meaning.

Particularly preferred compounds are those of the formula X in which A is a group of the formula —CH=CH—,

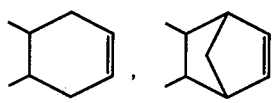

and especially

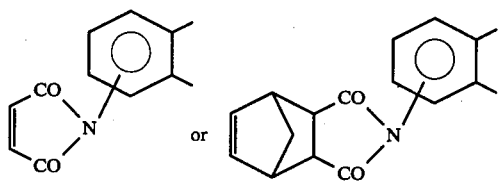

and Z is a 4,4'-diphenylmethane or 4,4'-diphenyl ether radical.

Possible bridge members Z are, especially, alkylene groups having 2-12 and especially 2-6 carbon atoms, phenylene or naphthylene groups which are unsubstituted or substituted by halogen atoms, such as chlorine, fluorine or bromine, or by alkyl or alkoxy groups having 1-4, and especially 1 or 2, carbon atoms, cyclohexylene groups and groups of the formulae

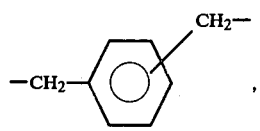

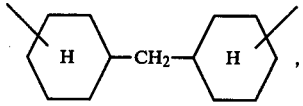

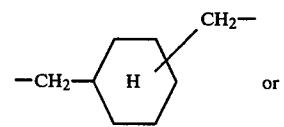

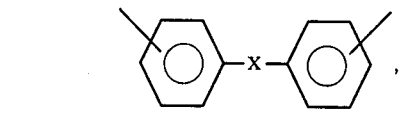

in which X is as defined under formula I.

However, oligoimides of the type described in German Offenlegungsschrift 2,230,874, or bis- and tris-imides of the formula XI

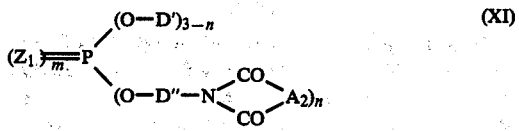

(XI)

can also be employed in the mixtures according to the invention. In formula XI, D' and D" are aromatic radicals which are unsubstituted or substituted or interrupted by an oxygen atom, an alkylene group or a sulphonyl group, $Z_1$ is an oxygen or sulphur atom, m is the number 1 or 0 and n is the number 2 or 3 and $A_2$ is a radical of the formulae

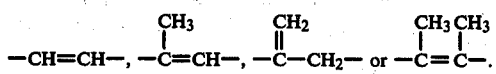

Examples of suitable polyimides which may be mentioned are: N,N'-ethylene-bis-maleimide, N,N'-hexamethylene-bis-nadicimide, N,N'-m- or -p-phenylene-bis-maleimide, N,N'-p-tolylene-bis-maleimide, N,N'-p-cyclohexylene-bis-1,2,3,6-tetrahydrophthalimide, N,N'-m- or -p-xylylene-bis-citraconimide, N,N'-hexamethylene-bis-3,6-endoxo-1,2,3,6-tetrahydrophthalimide, N,N',4,4'-dicyclohexylmethane-bis-maleimide, N,N',4,4'-diphenylmethane-bis-nadicimide, N,N',4,4'-diphenylmethane-bis-maleimide, N,N',4,4'-diphenyl ether -bis-maleimide, N,N',4,4'-diphenylsulphone-bis-maleimide, N,N',α,β',4,4'-dimethylenecyclohexane-bis-maleimide, N,N',4,4'-diphenylcyclohexane-bis-maleimide, N,N',4,4',2,2-diphenylpropane-bis-maleimide, N,N',γ,γ'-1,3-dipropylene-5,5-dimethyl-hydantoin-bis-maleimide, N,N',4,4'-diphenylmethane-bis-dimethyl-maleimide, N,N'-hexamethylene-bis-dimethylmaleimide, N,N',4,4'-diphenylmethane-bis-3-maleimidylphthalimide, N,N',4,4'-(diphenyl ether)-bis-3-nadicimidylphthalimide, N,N',4,4'-diphenylsulphone-bis-4-maleimidylphthalimide, the N,N'-bis-maleimide of 4,4'-diamino-triphenyl phosphate or of 4,4'-diamino-triphenyl thiophosphate and the N,N',N"-tris-maleimide of tris-(4-aminophenyl) phosphate.

Polyimides according to the definition can be obtained by methods which are known per se by reacting suitable diamines or polyamines with anhydrides of the formula (XII)

in which A is as defined.

Mixtures of two or more polyimides according to the definition and/or mixtures of different phthalimides of the formula I can also be used according to the invention.

The molar ratio of the phthalimide of the formula I to the polyimide according to the definition can vary within wide limits. Mixtures containing up to 50 mol percent, and preferably 5–30 mol percent, of phthalimide are appropriately used.

Depending on the intended use, cationic, anionic or free radical polymerisation initiators which are known per se can also be added to the mixtures according to the invention. In general, these polymerisation initiators are used in an amount of about 0.01 to 5 percent by weight, and preferably of 0.01 to 1.5 percent by weight, relative to the total weight of the reactants. Free radical initiators, such as inorganic or organic peroxides or azo compounds, for example hydrogen peroxide, potassium peroxydisulphate, tert.-butyl hydroperoxide, di-tert.-butyl peroxide, peracetic acid, benzoyl peroxide, diacyl peroxides, cumene hydroperoxide, tert.-butyl perbenzoate, tert.-alkyl peroxycarbonates and α,α'-azoisobutyronitrile, are preferred. In general, however, the addition of polymerisation initiators can be omitted.

The phthalimides of the formula I and the polyimides according to the definition are preferably reacted with one another in the melt or partly in the melt and partly in the solid phase. However, the reaction can also be carried out in solution. In most cases, however, the addition of organic solvents is superfluous because the starting mixtures as such already have an adequately low viscosity at temperatures above about 160° C. The reaction in the melt is appropriately carried out at temperatures between about 150° and 250° C. and preferably between 160° and 200° C.

Suitable organic solvents which can be used for the reaction in solution are, for example, dioxane, tetrahydrofurane, tetramethylurea, dimethylformamide, dimethylacetamide and N-methylpyrrolidone.

Processing of the mixtures according to the invention to crosslinked polymers containing imide groups can also be carried out in two stages. After mixing and, where appropriate, after subsequent grinding of the starting materials, the powder or the liquid is first heated to about 150°–220° C. for a limited period. During this period, a soluble prepolymer forms which is still thermoplastic. If desired, this prepolymer is again ground to a powder before further processing. However, the prepolymerisation can also be carried out by heating a solution or suspension of the starting materials in one of the abovementioned organic solvents. Subsequently, the prepolymers are finally cured by heating to temperatures between about 170° and 250° C.

The production of the crosslinked polymers containing imide groups is as a rule effected with simultaneous shaping to give mouldings, sheet-like structures, laminates, glue bonds, foams and the like. The additives commonly used in the technology of curable plastics, such as fillers, plasticisers, pigments, dyes, mould release agents and flame-retardant substances, can be added to the curable mixtures. Fillers which can be used are, for example, glass fibres, mica, graphite, quartz powder, kaolin, colloidal silicon dioxide or metal powders. Substances which can be used as mould release agents are, for example, silicone oil, various waxes, zinc stearate or calcium stearate and the like.

Shaping of the products which can be produced with the mixtures according to the invention can be effected in a very simple manner by the casting process using conventional casting moulds.

However, shaping can also be carried out by the hot pressing process using a press at temperatures between about 170° and 250° C. and under a pressure of about 100–450 kp/cm².

The polymers which can be produced with the mixtures according to the invention can be employed, in particular, in the fields of castings production, surface protection, the electrical industry, laminating processes, adhesives and foam production and in the building trade.

EXAMPLE 1

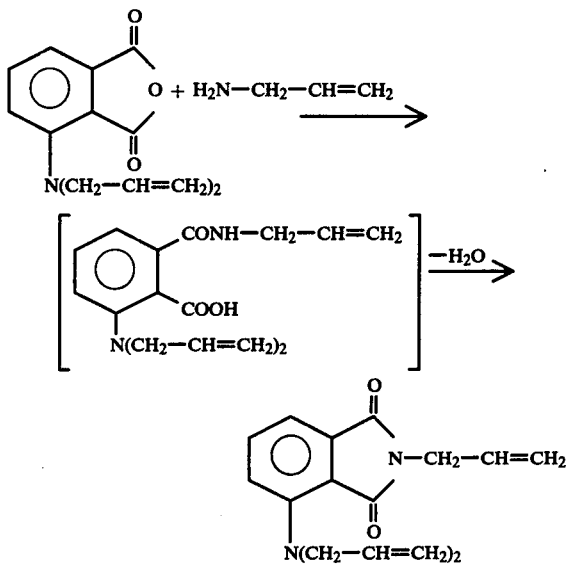

8.6 g (0.15 mol) of allylamine are added to a solution of 24.3 g (0.1 mol) of 3-N,N-diallylaminophthalic anhydride in 200 ml of toluene and the mixture is stirred for 2 hours at 75°–80° C. The toluene is then distilled off and the residue is stirred for 1 hour at 150°–160° C. The melt, which has solidified on cooling, is recrystallised from 120 ml of special boiling point gasoline (mixture of hydrocarbons; boiling point 110°–130° C.). Yield of 3-N,N-diallylaminophthalic acid allylimide: 17.6 g=81.5% of theory; melting point: 74° C.

Analysis for $C_{17}H_{18}N_2O_2$:
calculated: C 72.3%; H 6.4%; N 9.9%;
found: C 72.3%; H 6.5%; N 9.9%.

The 3-N,N-diallylaminophthalic anhydride used in the above example is prepared as follows: 225 g (1.0 mol) of disodium 3-aminophthalate and 138 g (1.0 mol) of potassium carbonate are dissolved in 400 ml of water. 317.2 g (2.6 mols) of allyl bromide are added to the solution at about 25° C. and the reaction mixture is stirred for 4 hours at 30°–35° C. Diallylaminophthalic acid is precipitated by adding 200 ml of 35% strength aqueous hydrochloric acid. The product is filtered off at 10° C., washed with 100 ml of water and dried. Yield: 222 g=85% of theory. 261 g (1 mol) of this 3-diallylaminophthalic acid are heated to 150°–155° C. A melt forms and this is stirred for 2 hours at about 150° C. while a stream of nitrogen is passed over and is then allowed to cool to 50° C. 750 ml of toluene and 750 ml of n-hexane are then added and the crude product is recrystallised from this mixture. This gives 237 g (95% of theory) of 3-N,N-diallylaminophthalic anhydride; melting point 94°–95° C.

EXAMPLE 2

If, in Example 1, the equivalent amount of n-propylamine is employed in place of 8.6 g of allylamine and in other respects the procedure is identical, this gives 3-N,N-diallylaminophthalic acid n-propylimide; melting point 65° C.

Analysis for $C_{17}H_{20}N_2O_2$:
calculated: C 71.8%; H 7.1%; N 9.9%;
found: C 71.6%; H 7.3%; N 9.9%.

EXAMPLE 3

If, in Example 1, the allylamine is replaced by the equivalent amount of aniline and in other respects the procedure is as indicated in the said example, this gives 3-N,N-diallylaminophthalic acid phenylimide; melting point 93° C.

Analysis for $C_{20}H_{18}N_2O_2$:
calculated: C 75.4%; H 5.7%; N 8.8%;
found: C 75.0%; H 5.8%; N 8.8%.

EXAMPLE 4

If, in Example 1, the 3-N,N-diallylaminophthalic anhydride is replaced by the equimolecular amount of 4-N,N-diallylaminophthalic anhydride and in other respects the procedure is identical, this gives 4-N,N-diallylaminophthalic acid allylimide. Since the product is still liquid at 20° C., it was purified by distillation.

Boiling point under 0.003 mm, 150°–170° C.
Analysis for $C_{17}H_{18}N_2O_2$:
calculated: C 72.3%; H 6.4%; N 9.9%;
found: C 72.5%; H 6.6%; N 9.6%.

EXAMPLE 5

If, in Example 1, the 3-N,N-diallylaminophthalic anhydride is replaced by a 1:1 mixture of 3- and 4-N,N-diallylaminophthalic anhydride, this gives a 1:1 mixture of isomers consisting of 3- and 4-N,N-diallylaminophthalic acid allylimide.

The product mixture is purified by distillation in a bulb tube oven; boiling point under 0.002 mm, 150°–170° C.
Analysis for $C_{17}H_{18}N_2O_2$:
calculated: C 72.3%; H 6.4%; N 9.9%;
found: C 72.2%; H 6.5%; N 10.0%.

EXAMPLE 6

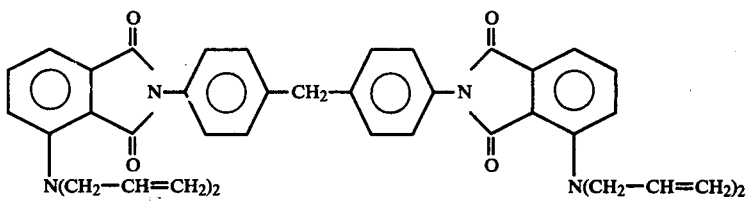

9.9 g (0.05 mol) of 4,4'-diaminodiphenylmethane are added to a solution of 24.3 g (0.1 mol) of 3-N,N-diallylaminophthalic anhydride in 250 ml of toluene and the mixture is allowed to react for 2 hours at 80°–85° C. All of the toluene is then distilled off, the residue is dissolved in 100 ml of acetic anhydride and the resulting solution is stirred for 30 minutes at 120°–125° C. After cooling, the product which has precipitated is filtered off and dried in vacuo. This gives 26 g (80% of theory) of bis-(4,4'-diphenylmethane)-3-N,N-diallylaminophthalimide of the above formula; melting point 178°–179° C.

Analysis for $C_{41}H_{36}N_4O_4$:
calculated: C 75.9%; H 5.6%; N 8.6%;
found: C 76.0%; H 5.9%; N 8.5%.

EXAMPLE 7

19.33 g (0.054 mol) of 4,4'-bis-maleimidyl-diphenylmethane (BMDM) and 1.69 g (0.006 mol) of the 3-diallylaminophthalic acid allylimide prepared according to Example 1 are mixed together well and the mixture is heated to 165° C. with occasional stirring. A melt forms and this is poured into an aluminium mould, which has been preheated to 180° C., in order to produce sheets 4 mm and 2 mm thick. Curing is effected in a circulating air oven for 16 hours at 180° C. This gives transparent, bubble-free castings, the physical, mechanical and electrical properties of which are summarised in Table I which follows. A lengthening of the pot life by about 60% is achieved by the addition of the above amount of the allyl derivative to the bis-imide.

EXAMPLES 8-14

Further castings are produced by the procedure described in Example 7. The molar ratios of the mixing components used, the curing conditions and the properties of the cured castings are summarised in Table I. In addition, the castings obtained according to Example 8 showed no decrease in the flexural strength after ageing for 300 hours at 240° C. in air.

and the mixture is heated to 178°-180° C. with occasional stirring. A melt of low viscosity forms after 3 minutes and this is kept at this temperature for 45 minutes. The gelled mixture which has formed at the end of this period is allowed to cool and is ground to a fine powder. For processing by the compression moulding process, this powder is introduced into a compression mould for circular sheets, which has been pre-heated to 215° C., and is subjected to compression moulding at this temperature for 60 minutes under a pressure of 350 kp/cm². A transparent, firm sheet is obtained. The electrical properties of the compression-moulded sheets are given in Table II.

EXAMPLES 16-18

Further compression mouldings are produced by the procedure described in Example 15. The molar ratios of the mixing components used, the processing conditions and the electrical properties of the resulting compression mouldings are summarised in Table II which follows.

Table II

| Example No. | Phthalimide according to Example No. | Molar ratio Phthalimide | Molar ratio BMDM | Pre-crosslinking conditions | Compression moulding conditions | $tg\delta \times 10^2$ (50 Hz) at (4) 180° C. | $tg\delta \times 10^2$ (50 Hz) at (4) 250° C. | $\epsilon$ (50 Hz) at (5) 180° C. | $\epsilon$ (50 Hz) at (5) 250° C. |
|---|---|---|---|---|---|---|---|---|---|
| 15 | 2 | 1 | 9 | 45 minutes/180° C. | 60 minutes/215° C. | 0.23 | 0.23 | 3.3 | 3.2 |
| 16 | 6 | 2 | 8 | 65 minutes/180° C. | 60 minutes/220° C. | 0.26 | 0.26 | 3.2 | 3.1 |
| 17 | 2 | 1 | 9 | 50 minutes/180° C. | 60 minutes/225° C. | 0.21 | 0.28 | 3.3 | 3.2 |
| 18 | 2 | 2 | 8 | 65 minutes/180° C. | 60 minutes/205° C. | 0.18 | 0.32 | 3.2 | 3.1 |

(4) and (5) c.f. Table I

EXAMPLE 19

9.08 g (0.014 mol) of 4,4'-bis-(3-maleimidylphthalimido)-diphenylmethane and 1.69 g (0.006 mol) of 3-N,N-diallylaminophthalic acid allylimide are mixed together well and the mixture is heated to 200° C., with occasional stirring. The mixture, which initially can be

Table I

| Example No. | Phthalimide according to Example No. | Molar ratio Phthalimide | Molar ratio BMDM | Curing conditions | Flexural strength N/mm² (1) | Deflection mm (2) | Absorption of water 4 days/ 23° C. in % (3) | $tg\delta \times 10^2$ (50 Hz) at (4) 180° C. | $tg\delta \times 10^2$ (50 Hz) at (4) 250° C. | $\epsilon$ (50 Hz) at (5) 180° C. | $\epsilon$ (50 Hz) at (5) 250° C. |
|---|---|---|---|---|---|---|---|---|---|---|---|
| 7 | 1 | 1 | 9 | 16 hours/180° C. | 86 | 2.5 | 1.0 | 0.26 | 0.42 | 3.5 | 3.5 |
| 8 | 1 | 2 | 8 | 16 hours/180° C. | 94 | 2.6 | 1.0 | | | | |
| 9 | 1 | 1 | 1 | 16 hours/180° C. | | | | 3.81* | 12.5** | 4.0 | 4.3 |
| 10 | 5 | 1 | 9 | 16 hours/180° C. | | | | 0.45 | 0.50 | 3.4 | 3.4 |
| 11 | 2 | 1 | 9 | 16 hours/180° C. | 59 | 1.5 | 1.0 | | | | |
| 12 | 3 | 2 | 8 | 16 hours/180° C. | 74 | 2.5 | 1.2 | | | | |
| 13 | 6 | 1 | 9 | 16 hours/180° C. | 79 | 2.2 | 0.9 | | | | |
| 14 | 6 | 2 | 8 | 16 hours/180° C. | 100 | 3.2 | 1.1 | | | | |

(1) Flexural strength according to VSM 77,103
(2) Deflection according to VSM 77,103
(3) Absorption of water, 4 days at 23° C.
(4) Dielectric loss factor tgδ according to DIN 53,483
(5) Dielectric constant ε according to DIN 53,483
VSM = Verein Schweizerischer Maschinenindustrieller
DIN = Deutsche Industrie-Norm
*200° C. instead of 180° C.
**240° C. instead of 250° C.

EXAMPLE 15

12.89 g (0.036 mol) of 4,4'-bis-maleimidyl-diphenylmethane (BMDM) and 1.14 g (0.004 mol) of the 3-N,N-diallylaminophthalic acid n-propylimide prepared according to Example 2 are mixed well together stirred easily, becomes noticeably more viscous during this period. After heating for 50 minutes at 200° C., the mixture is cooled and the prepolymer which has solidified is ground to a fine powder. For processing by the compression moulding process, this powder is introduced into a compression mould for circular sheets, which has been preheated to 220° C., and is subjected to compression moulding at this temperature for 60 minutes under a pressure of 450 kp/cm². A transparent, firm sheet is obtained, which, after heat treatment at 200° C. for 16 hours, has good electrical properties.

The 4,4'-bis-(3-maleimidyl-phthalimido)-diphenylmethane used in the above example can be prepared as follows:

91.89 g (0.378 mol) of 3-maleimidyl-phthalic anhydride (prepared by reacting 3-aminophthalic acid with maleic anhydride and subjecting the resulting 3-maleamidyl-phthalic acid to cyclisation with anhydrous sodium acetate and acetate anhydride, according to German Offenlegungsschrift 2,459,673) are dissolved in 343 ml of anhydrous N,N-dimethylacetamide under a nitrogen atmosphere in a sulphonation flask and the solution is cooled to 0°–5° C. A solution of 35.68 g (0.18 mol) of 4,4'-diaminodiphenylmethane in 200 ml of DMA is then allowed to run in dropwise, with stirring, and, after the addition is complete, the reaction mixture is stirred for a further 2 hours at 20°–25° C. 132 ml (1.44 mols) of acetic anhydride are then added and the solution is heated to 80° C. for 2 hours, with stirring. After cooling to about 20°–25° C., the reaction product is precipitated with water. The resulting precipitate is filtered off, washed several times with water and dried for 20 hours at 80° C. in a vacuum cabinet. The reaction product is then boiled in approximately ten times the amount by weight of ethanol for 20 minutes and the mixture is then filtered hot. After drying the product at 80° C. under a high vacuum, this gives 107 g of 4,4'-bis-(3-maleimidyl-phthalimido)-diphenylmethane in the form of a slightly yellowish powder; melting point 190°–210° C.

EXAMPLE 20

In accordance with the procedure described in Example 19, 5.19 g (0.008 mol) of 4,4'-bis-(3-maleimidyl-phthalimido)-diphenylmethane and 0.56 g (0.002 mol) of 3-N,N-diallylaminophthalic acid allylimide are reacted at 200° C. for 20 minutes. After processing the resulting prepolymer by the compression moulding process at 200°–220° C., as described in the preceding examples, transparent, firm sheets with good electrical properties are obtained.

EXAMPLE 21

1.84 g (0.004 mol) of 4,4'-bis-tetrahydrophthalimidyl-diphenyl ether, 0.28 g (0.001 mol) of 3-N,N-diallylaminophthalic acid allylimide and 0.18 g (0.0005 mol) of 4,4'-bis-maleimidyl-diphenylmethane are mixed well together and the mixture is heated to 215° C. in the course of 1 hour. After cooling, the fused mass is finely powdered and subjected to compression moulding in a platen press at 230° C. for 10 minutes under the contact pressure and for 1 hour under a pressure of 50 kg/cm², to give a sheet.

The 4,4'-bis-tetrahydrophthalimidyl-diphenyl ether used in the above example is prepared as follows: 29.82 g (0.2 mol) of tetrahydrophthalic anhydride are dissolved in 120 ml of anhydrous DMA and the solution is cooled to 0°–5° C. A solution of 20.02 g (0.1 mol) of 4,4'-diamino-diphenyl ether in 100 ml of DMA is then added dropwise, with stirring. After stirring for one hour at 20°–25° C., 70 ml of toluene are added and the reaction solution is heated under reflux until no further water can be separated off with the aid of a water separator. The toluene is then distilled off, the reaction solution is poured into water and the resulting precipitate is washed several times with water. After drying at 120° C. in a vacuum cabinet, this gives 44 g (96% of theory) of 4,4'-bis-tetrahydrophthalimidyl-diphenyl ether in the form of a yellowish powder.

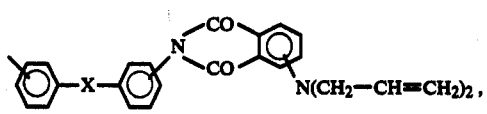
X is —CH$_2$— or —O—, R$_2$ is —CH$_2$—CH=CH$_2$ and R$_3$ is hydrogen.
3. A compound according to claim 1 of the formula
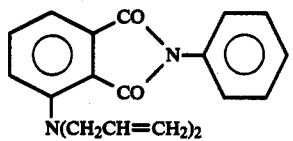
4. A compound according to claim 1 of the formula
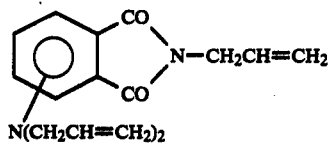
5. A compound according to claim 1 of the formula
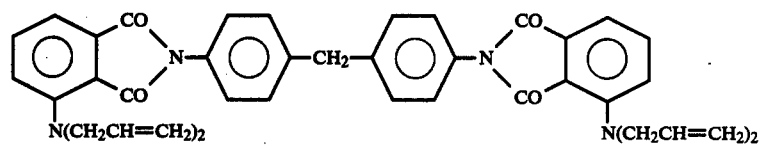

What is claimed is:

1. A phthalidimide of the formula I

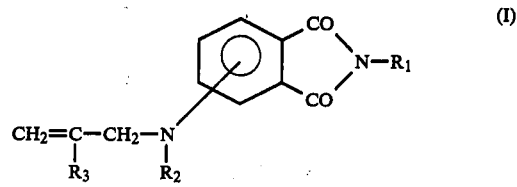

in which $R_1$ is alkyl having 1 to 12 carbon atoms, alkenyl having 2 to 5 carbon atoms, phenyl; phenyl substituted by halogen, by alkyl of 1 to 4 carbon atoms or by alkoxy of 1 to 4 carbon atoms; naphthyl, alkylene-Y having 2 to 12 carbon atoms in the alkylene part, arylene-Y in which arylene is phenylene; phenylene substituted by halogen, by methyl or by methoxy; or naphthylene, or a grouping

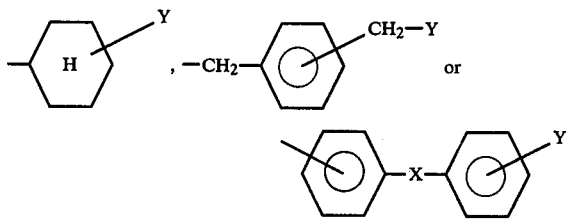

in which X is $-CH_2-$, $-S-$, $-SO-$, $-SO_2-$, $-O-$ or

and Y is a grouping

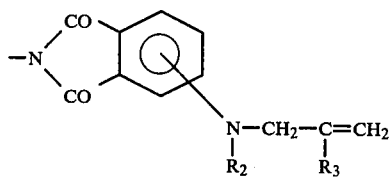

$R_2$ is hydrogen or

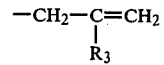

and $R_3$ is hydrogen or methyl.

2. A compound of the formula I according to claim 1, in which $R_1$ is alkyl having 1–4 carbon atoms, allyl, phenyl or a grouping